(12) United States Patent
Gilmour et al.

(10) Patent No.: US 9,475,773 B2
(45) Date of Patent: Oct. 25, 2016

(54) NK3 RECEPTOR ANTAGONIST COMPOUND (NK3RA) FOR USE IN A METHOD FOR THE TREATMENT OF POLYCYSTIC OVARY SYNDROME (PCOS)

(71) Applicant: ASTRAZENECA AB, Sodertalje (SE)

(72) Inventors: Peter Stewart Gilmour, Macclesfield (GB); Tony Ho, Wilmington, DE (US); Rahul Kakkar, Waltham, MA (US); Lorraine Webber, Macclesfield (GB)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 14/785,285

(22) PCT Filed: Apr. 14, 2014

(86) PCT No.: PCT/GB2014/051156
§ 371 (c)(1),
(2) Date: Oct. 16, 2015

(87) PCT Pub. No.: WO2014/170648
PCT Pub. Date: Oct. 23, 2014

(65) Prior Publication Data
US 2016/0083350 A1    Mar. 24, 2016

Related U.S. Application Data

(60) Provisional application No. 61/813,699, filed on Apr. 19, 2013.

(51) Int. Cl.
| | | |
|---|---|---|
| A61K 31/47 | (2006.01) | |
| C07D 215/52 | (2006.01) | |
| A61K 47/20 | (2006.01) | |
| A61K 47/26 | (2006.01) | |
| A61K 47/12 | (2006.01) | |
| A61K 47/38 | (2006.01) | |
| A61K 9/20 | (2006.01) | |

(52) U.S. Cl.
CPC ........... *C07D 215/52* (2013.01); *A61K 9/2013* (2013.01); *A61K 9/2018* (2013.01); *A61K 9/2054* (2013.01); *A61K 31/47* (2013.01); *A61K 47/12* (2013.01); *A61K 47/20* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | |
|---|---|---|
| 5,177,096 A | 1/1993 | Keenan et al. |
| 5,248,689 A | 9/1993 | Girard et al. |
| 5,444,081 A | 8/1995 | Gleason et al. |
| 5,686,455 A | 11/1997 | Adams et al. |
| 5,811,553 A | 9/1998 | Farina et al. |
| 5,942,523 A | 8/1999 | Bichon et al. |
| 6,057,362 A | 5/2000 | Yamashita |
| 6,232,342 B1 | 5/2001 | Carr et al. |
| 6,277,862 B1 | 8/2001 | Giardina et al. |
| 6,387,898 B1 | 5/2002 | Feuerstein |
| 6,608,083 B1 | 8/2003 | Farina et al. |
| 6,743,804 B2 | 6/2004 | Giardina et al. |
| 6,858,630 B2 | 2/2005 | Luengo et al. |
| 7,253,286 B2 | 8/2007 | Funahashi et al. |
| 7,608,628 B2 | 10/2009 | Simpson et al. |
| 8,071,621 B2 * | 12/2011 | Simpson ............... C07D 215/14 514/313 |
| 2003/0195204 A1 | 10/2003 | Giardina et al. |
| 2004/0006135 A1 | 1/2004 | Sobolov-Jaynes et al. |
| 2007/0254886 A1 | 11/2007 | Habashita et al. |
| 2008/0200504 A1 | 8/2008 | Albert et al. |
| 2008/0293765 A1 | 11/2008 | Albert et al. |
| 2013/0023530 A1 | 1/2013 | Hoveyda et al. |

FOREIGN PATENT DOCUMENTS

| | | |
|---|---|---|
| EP | 0 940 391 A2 | 9/1999 |
| EP | 1 192 952 A2 | 4/2002 |
| EP | 0 804 419 B1 | 8/2003 |
| WO | 95/32948 A1 | 12/1995 |
| WO | 96/02509 A1 | 2/1996 |

(Continued)

OTHER PUBLICATIONS

Albert, "Nuerokinin antagonists and their potential role in treating depression and other stress disorders," *Expert Opin. Ther. Patents* 14(10):1421-1433, 2004.

(Continued)

*Primary Examiner* — Brian J Davis
(74) *Attorney, Agent, or Firm* — Seed IP Law Group PLLC

(57) ABSTRACT

A method for treating polycystic ovarian syndrome and related conditions with a compound (I): or a pharmaceutically acceptable salt thereof.

(1)

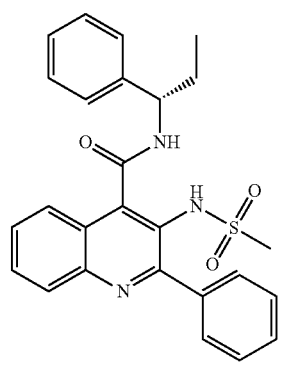

1 Claim, 3 Drawing Sheets

(56) References Cited

FOREIGN PATENT DOCUMENTS

| WO | 97/19926 A1 | 6/1997 |
|---|---|---|
| WO | 97/19927 A1 | 6/1997 |
| WO | 97/19928 A1 | 6/1997 |
| WO | 97/21680 A1 | 6/1997 |
| WO | 99/51565 A1 | 10/1999 |
| WO | 00/12497 A2 | 3/2000 |
| WO | 00/31037 A1 | 6/2000 |
| WO | 00/43008 A1 | 7/2000 |
| WO | 00/64877 A1 | 11/2000 |
| WO | 02/13825 A1 | 2/2002 |
| WO | 02/38548 A1 | 5/2002 |
| WO | 02/094187 A2 | 11/2002 |
| WO | 04/000355 A1 | 12/2003 |
| WO | 2004/050626 A1 | 6/2004 |
| WO | 2004/050627 A1 | 6/2004 |
| WO | 2004/087153 A2 | 10/2004 |
| WO | 2005/014532 A1 | 2/2005 |
| WO | 2005/014533 A2 | 2/2005 |
| WO | 2005/014534 A1 | 2/2005 |
| WO | 2005/094801 A1 | 10/2005 |
| WO | 2005/108359 A1 | 11/2005 |
| WO | 2006/120478 A2 | 11/2006 |
| WO | 2006/137789 A1 | 12/2006 |
| WO | 2007/022059 A2 | 2/2007 |
| WO | 2007/069977 A1 | 6/2007 |
| WO | 2008/021388 A1 | 2/2008 |
| WO | 2006/050991 A1 | 5/2009 |
| WO | 2011/121137 A1 | 10/2011 |

OTHER PUBLICATIONS

Albert et al., "Neurokinin-3 receptor antagonists in schizophrenia," *Expert Opin. Ther. Patents* 16(7): 925-937, 2006.

Banker et al., *Modern Pharmaceutics*, New York, Marcel Dekker Inc., 1996, pp. 451 and 596, 3 pages.

Giardina et al., "Discovery of a Novel Class of Selective Non-Peptide Antagonists for the Human Neurikinin-3 Receptor. 2. Identification of (S)-N-(1-Phenylpropyl)-3-hydroxy-2-phenylquinoline-4-carboxamide (SB 223412)," *Journal of Med. Chem.* 42:1053-1065, 1999.

Hall et al., "Insights into hypothalamic-pituitary dysfunction in polycystic ovary syndrome," *J Endocrinol. Invest.* 21(9):602-611, Oct. 1998.

Liu et al., "Sensitivity and specificity of pulse detection using a new deconvolution method," *Am J Physiol Endocrinol Metab* 297:E538-E544, Jun. 2009.

Losco et al., "Administration of an Antagonist of Neurokinin Receptors 1, 2 and 3 Results in Reproductive Tract Changes in Beagle Dogs, but Not Rats," *Toxicologic Pathology* 35:310-322, 2007.

Malherbe et al., "Tachykinin neurokinin 3 receptor antagonists: patent review (2005-2010)," *Expert Opin. Ther. Patents* 21(5):637-655, 2011.

Noritake et al., "Involvement of Neurokinin Receptors in the Control of Pulsatile Luteinizing Hormone Secretion in Rats," *Journal of Reproduction and Development* 57(3):409-415, 2011.

Patani et al., "Bioisosterism: A Rational Approach in Drug Design," *Chem. Rev.* 96:3147-3176, 1996.

Simpson et al., "Discovery of AZD2624: a potent and selective NK3 antagonist to test the NK3 hypothesis in schizophrenia," *Division of Medicinal Chemistry Scientific Abstracts for the 239th National Meeting and Exposition*, Mar. 21-25, 2010, 330 pages.

Veldhuis et al., "Motivations and Methods for Analyzing Pulsatile Hormone Secretion," *Endocrine Reviews* 29(7):823-864, Dec. 2008.

Wolff, *Burger's Medicinal Chemistry and Drug Discovery: Principles and Practice*, New York, John Wiley & Sons Inc., Feb. 8, 1995, pp. 975-977, 4 pages.

Xiong et al., "Synthesis and SAR of sulfoxide substituted carboxyquinolines as NK3 receptor antagonists," *Bioorganic & Medicinal Chemistry Letters* 21:1896-1899, 2011.

\* cited by examiner

PKPD model scheme of NK3RA

Predicted steady state NK3RA concentration after administering 40mg BID or 80mg QD of NK3RA.*

*Note: the mean weight of subjects in the simulation dataset is same as the mean from the present study cohorts at 77 Kg.

Predicted steady state testosterone concentration after administering 40mg BID or 80mg QD of NK3RA.

(A)
40mg BID = Red Line
90%CI = Blue Line (B)
80mg QD = Red Line
90%CI = Blue Line

| 1 = Blue Line |
| 2 = Red Line |
| 3 = Blue Line |

NK3 RECEPTOR ANTAGONIST COMPOUND (NK3RA) FOR USE IN A METHOD FOR THE TREATMENT OF POLYCYSTIC OVARY SYNDROME (PCOS)

FIELD OF THE INVENTION

This invention is directed to the treatment of polycystic ovarian syndrome (PCOS) and related conditions.

BACKGROUND OF THE INVENTION

Polycystic ovarian syndrome (PCOS) is a condition that afflicts certain women. Hormonally, the disease may be characterized by an elevation in serum androgens. This elevation is thought to be the proximate cause for the PCOS phenotype of hyperandrogenism (acne and hirsutism) which typifies these patients, as well as possibly contributing to features of central adiposity and insulin resistance. The elevation of serum androgens, along with the hallmark phenotype of anovulation and infertility, has been traced to an elevation in serum luteinizing hormone (LH) levels, increased LH pulse frequency, and/or increased serum LH/follicle stimulating hormone (FSH) ratio (See Hall J E, J Endocrinol Invest. 1998 October; 21(9):602-11).

At the time of filing there are no approved treatments for PCOS. "Off-label" therapies currently prescribed are aimed at eliminating the symptoms of androgen excess. First-line treatment of PCOS is usually the oral contraceptive pill (OCP) for women in whom fertility is not immediately desired. However, approximately half of these patients fail to achieve adequate control of their androgenic symptoms with an OCP and require add-on anti-androgen therapy. Anti-androgen therapy is most commonly delivered as high-dose spironolactone, which carries the risk of potentially harmful electrolyte derangement. GnRH analogues are used as the next line of therapy to reduce androgen levels, but given their marked potency they often induce chemical menopause, and therefore require add-back hormonal therapy. In addition to treatment with a therapy to reduce androgen levels, metformin may be administered as it is believed to improve menstrual regularity and fertility (as well as insulin resistance). However, data on its efficacy in these endpoints is inconclusive. For women trying to conceive, additional treatment with clomiphene (+/− metformin) improves conception rates, but with the associated risks of ovarian hyperstimulation and multiple pregnancies.

Therefore, in light of current "off-label" symptom-driven therapy with limited efficacy and notable side effects, there is a need for an approach that specifically targets the underlying hypothalamic-pituitary-gonadal (HPG) pathophysiology of PCOS and modulates LH pulsatility, with the goal of affording disease modification and concomitant symptom relief without significant adverse effects.

BRIEF SUMMARY OF THE INVENTION

Accordingly, we believe therapies that target the underlying HPG pathophysiology of PCOS and modulate LH pulsatility may be useful in treating PCOS. Furthermore, we believe that the NK3 receptor antagonist, 3-(methanesulfonamido)-2-phenyl-N-[(1S)-1-phenylpropyl]quinoline-4-carboxamide (NK3RA):

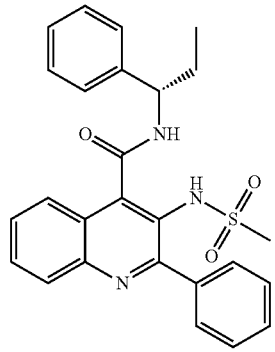 [SMILES: CC[C@H](NC(=O)c1c(NS(C)(=O)=O)c(-c2ccccc2)nc2ccccc12)c1ccccc1]

and pharmaceutically-acceptable salts thereof, are useful in the modulation of LH pulsatility. One aspect of the invention is NK3RA and pharmaceutically-acceptable salts thereof for use in the modulation of LH pulsatility. Another aspect of the invention is NK3RA and pharmaceutically-acceptable salts thereof for use in the treatment of conditions in which modulation of LH pulsatility is beneficial. A further aspect of the invention is NK3RA and pharmaceutically-acceptable salts thereof for use in the treatment of PCOS.

DETAILED DESCRIPTION

Figure 1:
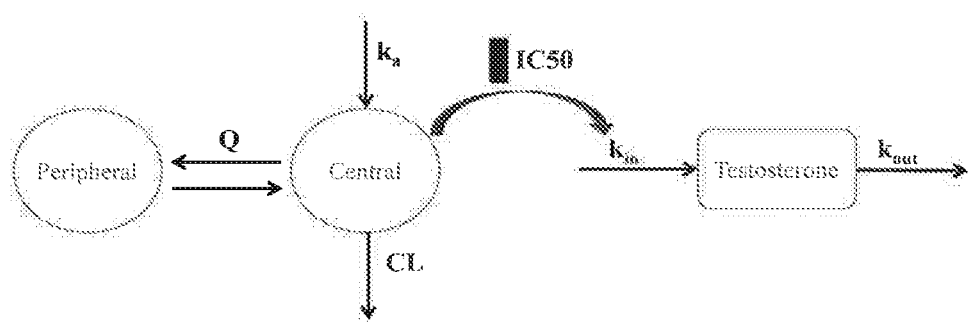
FIG. 1 is the PKPD model scheme of NK3RA.

In addition to the aspects noted above, a further aspect of the invention is NK3RA for use in the modulation of LH pulsatility. Another aspect of the invention is NK3RA for use in the treatment of conditions in which modulation of LH pulsatility is beneficial. A further aspect of the invention is NK3RA for use in the treatment of PCOS.

Furthermore, current therapies that only treat symptoms derived from elevated androgen levels result in some of the symptoms of PCOS remaining untreated. We believe, that NK3RA and pharmaceutically-acceptable salts thereof target the fundamental pathophysiology of the disease and may have the potential to treat symptoms not immediately derived from elevated androgen levels. Examples of these symptoms include amenorrhea, oligomenorrhea and anovulation. NK3RA pharmaceutically-acceptable salt thereof may also be useful in restoring fertility.

Accordingly another aspect of the invention relates to the use of NK3RA or a pharmaceutically-acceptable salt thereof in the treatment of amenorrhea in PCOS. Another aspect of the invention relates to the use of NK3RA or a pharmaceutically-acceptable salt thereof in the treatment of oligomenorrhea in PCOS. Yet another aspect of the invention relates to the use of NK3RA or a pharmaceutically-acceptable salt thereof in the treatment of anovulation in PCOS. Yet another aspect of the invention relates to the use of NK3RA or a pharmaceutically-acceptable salt thereof for the restoration of fertility.

Another aspect of the invention relates to the use of NK3RA or a pharmaceutically-acceptable salt thereof in the manufacture of a medicament for modulating LH pulsatility. A further aspect of the invention relates to the use of NK3RA or a pharmaceutically-acceptable salt thereof in the manufacture of a medicament for the treatment of PCOS.

A further aspect of the invention relates to a method of modulating LH pulsatility in a patient in need thereof, comprising administering to said patient a therapeutically effective amount of NK3RA or a pharmaceutically acceptable salt thereof.

Another aspect of the invention relates to a method of treating PCOS in a patient in need thereof, comprising administering to said patient a therapeutically effective amount of NK3RA or a pharmaceutically acceptable salt thereof.

Another aspect of the invention relates to the use of NK3RA in the manufacture of a medicament for modulating LH pulsatility. A further aspect of the invention relates to the use of NK3RA in the manufacture of a medicament for the treatment of PCOS.

A further aspect of the invention relates to a method of modulating LH pulsatility in a patient in need thereof, comprising administering to said patient a therapeutically effective amount of NK3RA.

Another aspect of the invention relates to a method of treating PCOS in a patient in need thereof, comprising administering to said patient a therapeutically effective amount of NK3RA.

Accordingly another aspect of the invention relates to the use of NK3RA in the treatment of amenorrhea in PCOS. Another aspect of the invention relates to the use of NK3RA in the treatment of oligomenorrhea in PCOS. Yet another aspect of the invention relates to the use of NK3RA in the treatment of anovulation in PCOS.

A further aspect of the invention is NK3RA and pharmaceutically-acceptable salts thereof for use in lowering testosterone in a woman suffering from PCOS. A further aspect of the invention is NK3RA for use in lowering testosterone in a woman suffering from PCOS.

A further aspect of the invention relates to the use of NK3RA or a pharmaceutically-acceptable salt thereof in the manufacture of a medicament for lowering testosterone levels in a woman suffering from PCOS. A further aspect of the invention relates to the use of NK3RA or a pharmaceutically-acceptable salt thereof in the manufacture of a medicament for lowering testosterone levels in a woman suffering from PCOS.

Another aspect of the invention relates to a method for lowering testosterone in a woman suffering from PCOS, comprising administering to said patient a therapeutically effective amount of NK3RA or a pharmaceutically acceptable salt thereof. Yet another aspect of the invention relates to a method of lowering testosterone in a woman suffering from PCOS, comprising administering to said patient a therapeutically effective amount of NK3RA.

A method of restoring fertility in a patient in need thereof, comprising administering to said patient a therapeutically effective amount of NK3RA or a pharmaceutically acceptable salt thereof.

A method of treating PCOS comprising the step of determining whether the testosterone level of a biological sample taken from a patient is higher than the normal level and, if it is, treating said patient with a therapeutically effective amount of NK3RA, or a pharmaceutically acceptable salt thereof.

NK3RA or a pharmaceutically acceptable salt thereof may be of use in the prevention of any of the conditions mentioned hereinabove.

NK3RA or pharmaceutically acceptable salts thereof may also be of use in treating the following: precocious puberty, endometriosis, heavy menstrual bleeding, uterine fibroids, pre-eclampsia, androgenic acne, benign prostatic hyperplasia and/or androgenic alopecia.

Examples of pharmaceutically-acceptable salts are known in the art. In one aspect, the pharmaceutically-acceptable salt of NK3RA is an acid addition salt. In another aspect, NK3RA may be used as the free base.

The synthesis of 3-(methanesulfonamido)-2-phenyl-N-[(1S)-1-phenylpropyl]quinoline-4-carboxamide is described in patent application publication WO 2007/069977, the disclosure of which is incorporated herein in its entirety by reference. It may also be prepares according to example 1.

The NK3RA may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

Preferably, administration will be orally by ingestion.

The quantity of the NK3RA to be administered will vary for the patient being treated and will vary from about 100 ng/kg of body weight to 100 mg/kg of body weight per day. However, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

Preferably the quantity of the NK3RA to be administered will vary for the patient being treated and will vary from about 5 mg to 100 mg per day.

In another aspect, the invention relates to a pharmaceutical composition comprising as active ingredient a therapeutically effective amount of the NK3RA according to the present invention, or a pharmaceutically acceptable salt thereof, in association with at least one pharmaceutically acceptable excipient, carrier or diluent.

In another aspect the invention relates to a pharmaceutical composition comprising:
the compound NK3RA;
mannitol and microcrystalline cellulose;
croscarmellose sodium,
hydroxypropyl cellulose,
sodium lauryl sulphate, and
magnesium stearate.

In one aspect, the dose of NK3RA according to the present invention, or a pharmaceutically acceptable salt thereof, may be administered once a day. Population pharmacokinetic and pharmacodynamic analysis demonstrates that NK3RA administered twice a day is better than once a day to maximally suppress testosterone during the entire dosing interval. In another aspect, the dose of NK3RA according to the present invention, or a pharmaceutically acceptable salt thereof, may be administered twice a day. In one aspect there is a period of at least 2 hours between the 2 doses taken in the same day. In another aspect there is a period of at least 4 hours between the 2 doses taken in the same day. In another aspect there is a period of at least 6 hours between the 2 doses taken in the same day. In another aspect there is a period of at least 8 hours between the 2 doses taken in the same day. In another aspect there is a period of at least 10 hours between the 2 doses taken in the same day. In one aspect the total daily dosage is in the range 20 mg to 180 mg of NK3RA. In another aspect the total daily dosage is in the range 40 mg to 80 mg of NK3RA. In another aspect the total daily dosage is in the range 70 mg to 90 mg of NK3RA. In another aspect the total daily dosage is about 80 mg of NK3RA. In another aspect the total daily dosage is about 80 mg of NK3RA administered as a 40 mg dose twice a day.

The treatment of PCOS defined herein may be applied as a mono therapy or may involve, in addition to the NK3RA, conjoint treatment with conventional therapy of value in treating PCOS. Such conventional therapy may include one or more of the following therapies currently prescribed that are aimed at eliminating the symptoms of androgen excess.

First-line treatment of PCOS is usually the oral contraceptive pill (OCP) for women in whom fertility is not immediately desired. However, approximately half of these patients fail to achieve adequate control of their androgenic symptoms with an OCP and require add-on anti-androgen therapy (commonly high-dose spironolactone). GnRH analogues are used as the next line of therapy, but require add-back hormonal therapy for women to avoid menopausal symptoms and the associated risks of exuberant GnRH antagonism. Metformin may also be used, as it is believed by some to improve menstrual regularity and fertility (as well as insulin resistance), although data on its efficacy in these endpoints is inconclusive. For women trying to conceive, clomiphene (+/− metformin) improves conception rates but with the associated risks of ovarian hyperstimulation and multiple pregnancies.

Such conjoint treatment may be achieved by way of the simultaneous, sequential or separate dosing of the individual components of the treatment.

Additional conventional therapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ NK3RA within the dosage range described herein and the other pharmaceutically active compound or compounds within approved dosage ranges and/or the dosage described in the publication reference.

Both non-clinical and clinical data on NK3RA have been obtained when it was being developed for use in the treatment of schizophrenia and some of which are described herein. Also see, Expert Opin. Ther. Patents (2011) 21(5): 637-655 and Simpson T R, Gadient R, Li Y, et al. Discovery of AZD2624: a potent and selective NK3 antagonist to test the NK3 hypothesis in schizophrenia Abstracts of Papers, 239th ACS National Meeting; 21-25 Mar. 2010. MEDI-35; San Francisco, Calif., USA Non-Clinical Pharmacology of NK3 RA:

The activity of a compound in antagonising the hrNK3 receptor expressed in CHO cells may be measured in the following Intracellular Calcium Mobilisation Assay:

CHO-K1 cells stably transfected with human recombinant Neurokinin-3 receptor (hrNK3 CHO-K1) were cultured in T225 cm$^3$ tissue culture flasks as monolayers in complete Ham's F-12 media (supplemented with 10% (v/v) FBS, 2 mM L-glutamine and 50 mg/ml Hygromycin B). Cultures are maintained under standard tissue culture conditions. For experiments, PBS was used to wash cells free of culture media and Trypsin was used to detach cells from the flask surface. Cells were counted, pelleted by centrifugation (100 g for 5 min) and resuspended in cell plating medium (UltraCULTURE by BioWhittaker 12-725F containing 200 mM L-Glutamine). The cells were pipetted into black walled, 384-well plate (clear bottom, poly-d-lysine coated plate (Biocoat, Becton Dickinson) at 10,000 cells per well and maintained under standard tissue culture conditions overnight.

Changes in intracellular free calcium were measured fluorometrically by loading hrNK3 CHO-K1 in 384-well plates with the calcium sensitive fluorescent dye, Fluo-4AM as described previously (Xiong et. al., *Bioorg. Med. Chem. Lett.* 2011, 21, 1896). Briefly, cells were loaded for 1 hour at 37° C. in assay buffer (Hanks' Balanced Salt Solution containing 15 mM HEPES and 2.5 mM Probenecid) containing 4.4 µM Fluo-4AM (dissolved in 10% (w/v) Pluronic F-127 in DMSO). Following dye loading procedure, assay buffer containing Fluo-4 AM was removed and replaced with assay buffer alone.

A test compound was pre-dissolved in DMSO and incubated with cells to a final concentration of 0.1% (v/v) DMSO for 15 minutes. Assays were initiated by the addition of Senktide (purchased from Bachem) and the transient increase in Fluo-4-fluorescence monitored using a FLIPR (Fluorometric Imaging Plate Reader, Molecular Devices, Sunnyvale, U.S.A.).

NK3RA was tested and found to be an antagonist of the hrNK3 receptor expressed in CHO cells.

Xiong H., Kang J., Woods J M., McCauley J P., Koether G M., Albert J S., Hinkley L., Li Y., Gadient R A., Simpson T R. Synthesis and SAR of sulfoxide substituted carboxyquinolines as NK3 receptor antagonists. *Bioorg. Med. Chem. Lett.* 2001, 21, 1896-1899

NK3RA is a potent and specific antagonist of the NK3 receptor. In vitro target engagement shows an IC50 2.24±0.57 nM (n=12), and specificity for NK3 over the other tachykinin receptors, NK1 and NK2, greater than 1200 and 800 fold respectively.

Safety pharmacology studies were carried out on NK3RA and included tests to investigate possible effects on the central nervous system (CNS), cardiovascular system, and respiratory system. In a neurobehavioral test battery in mice, oral doses of The NK3RA (100, 300, and 600 mg/kg [218, 653, and 1306 µmol/kg]) produced transient deficits in gait and spontaneous motor activity, with full recovery apparent within 24 hours. There were no significant findings in the modified rat Irwin test after oral treatment with The NK3RA at 46, 460, and 2022 mg/kg.

The NK3RA was only weakly active at the hERG channel in vitro, with slight (25%) inhibition of the hERG tail current at 97 µM. The NK3RA was without effect on the monophasic action potential of the guinea pig heart with IV doses up to 46 mg/kg (100 µmol/kg). A dog study that involved electrocardiographic (ECG) telemetry measurements showed that NK3RA treatment caused transient dose-related reductions in heart rate up to 29% at the highest dose tested (2000 mg/kg orally [4352 µmol/kg]). No other ECG parameter, including QTc interval duration, was affected in dogs, and there was no effect seen on blood pressure. The NK3RA had no cardiovascular effects in rats at 46 mg/kg orally (100 µmol/kg), the highest dose tested.

The NK3RA did not affect any respiratory parameters in rats up to 2000 mg/kg (4400 µmol/kg).

The NK3RA showed no activity in a rat cocaine drug discrimination assay at oral doses up to 46 mg/kg.

Pharmacokinetics and Product Metabolism in Animals:

The NK3RA was absorbed at a moderate rate in rats and more rapidly absorbed in dogs following oral administration. At low doses, the estimated $Cl_p$ of The NK3RA was moderate in rat (8.3 ml/min/kg) and low in the dog (1.2 ml/min/kg). Bioavailability (F) was ~100% in both species indicating extensive absorption in these species. The volume of distribution ($V_z$) was moderate (1.6 L·kg in rat and 0.81 L/kg in dog) and consistent with the physico-chemical properties of the compound. The elimination half-life (T½) ranged from 3.2 h (rat) to 9.5 h (dog). A secondary peak in plasma concentration was observed for some dogs after single or multiple dosing, possibly due to delayed absorption or enterohepatic recycling. Exposure increased with increasing dose of The NK3RA, although the increases were less than dose proportional. The NK3RA exposure decreased after multiple dosing in rats, indicating either changes in absorption or induction of The NK3RA metabolism, or both, after multiple dosing. Elimination of NK3RA in the dog was not complete by 72 hours; however, no accumulation or reduction of NK3RA was observed after a 28-day repeat dosing regimen. $T_{1/2}$ values ranged from 5.6 hours to 14.3 hours at the end of dosing for dogs dosed at 1000 mg/kg/day (2180 µmol/kg/day). There were no consistent sex differences observed in the exposure to NK3RA in these 2 species.

Following oral administration of The NK3RA in the rat, a pharmacologically active ketone metabolite appeared rapidly in plasma but slowly reached maximum concentration levels in all animals. Moderate accumulation of the metabolite was observed after multiple dosing with the NK3RA in both rats and dogs. The area under the plasma concentration-time curve from time 0 to 24 hours (AUC(0-24)) metabolite-to-parent ratios were relatively constant with the increase in dose within each day, but increased after multiple doses of the NK3RA, ranging from 0.731 to 1.97 in the rat and from 0.0880 to 0.196 in the dog, indicating that the NK3RA was highly metabolized in the rat and moderately in the dog. $T_{1/2}$ values ranged from 8.51 hours to 13.8 hours on Day 27 and Day 28 for dogs dosed with 1000 mg/kg/day (2180 µmol/kg/day) of the NK3RA. There were no consistent sex differences observed in the exposure to the metabolite in these 2 species.

Toxicology in Animals:

The NK3RA was well tolerated following single dosing up to the limit dose of 2000 mg/kg in rats and dogs, and following multiple dosing for three month up to 2000 mg/kg/day in rats and up to 1000 mg/kg/day in dogs. In rats, the highest doses produced a few clinical observations and increased liver weights with no histological correlate.

In dogs, the testis, epididymis, and prostate were target organs in males. In female dogs, ovarian uterine weights were reduced in treated animals. Increased liver weights were seen at mid and high doses and hepatobiliary toxicity in one high dose male. Thyroid weights were increased in the high dose group females. No other target organs have been identified.

Changes in the reproductive organ in the general toxicity and reproductive toxicity studies are entirely consistent with perturbation of regulatory hormones in animals with normal hormone homeostatic control.

Reproductive Organ Observations in Animals:

In the rat 3 month study relative testis weight was lower than controls at 200 and 2000 mg/kg/day (dose-related) and absolute weight was lower at 2000 mg/kg/day. Relative epididymis weight was lower at 2000 mg/kg/day. There were no NK3RA-related histological changes.

In the dog, the testis, epididymis and prostate weights were target organs, and no NOEL was established because effects were seen at all dose levels investigated in the study. Following the recovery period, weights of the testes had only partially returned to control values, while epididymis and prostate were comparable to controls. Epididymides and prostate glands had gained maturity, but aspermia was present in all dogs and testicular immaturity remained. Although the sexual maturity of the dogs at study start was not known, the findings are suggestive of delayed maturity at least in the 1 month study.

Plasma testosterone levels were shown to be very low within by 4 hours following dosing, virtually totally suppressed throughout the study, and were returning to normal levels by 48 to 72 hours after a final dose. Treatment of dogs with an antagonist of NK-1, -2 and -3, produced a similar effect (Losco et al Toxicol. Pathol. 2007; 35: 310-322). Reduced testis, epididymis and prostate weights were seen, with atrophy of all three organs with epididymal oligospermia or aspermia and epithelial apoptosis and vacuolation. Similar effects were not seen in the rat. The authors considered the observations in the dog to be the result of NK-3-mediated suppression of gonadotropin releasing hormone or luteinizing hormone (LH) and not a direct effect on the organs, because although a secondary effect of NK antagonism on the tissues could not be ruled out, there were no species-specific differences in toxicokinetics that could explain the dog-specific observations The antagonist of NK-1, -2 and -3, also produced reduced uterine and ovary weights and uterine and ovarian immaturity.

During the 3-month study with NK3RA reductions in ovarian and uterine weights and an increased incidence of anestrus were observed in female dogs, with complete recovery seen following 3 months off-dose. In rats, there were no findings in the female reproductive system during the repeat-dose toxicology studies with NK3RA. Disturbed estrus cycles were seen with no adverse effects on mating performance or fertility in the rat female fertility and embryofetal development study.

In female rats the No Adverse Effect Dose Level for fetal minor abnormalities and variants was 1000 mg/kg/day.

In female rabbits, the no effect dose level for maternal toxicity was 25 mg/kg/day. The no adverse effect dose level for fetal observations was 50 mg/kg/day.

Pharmacokinetics, Metabolism and Pharmacodynamics in Humans:

Pharmacokinetic properties have been investigated in healthy male subjects. The NK3RA was quickly absorbed following oral dosing. The elimination half-life for the NK3RA was approximately 7 hours. Both the area under the curve (AUC) and maximum plasma concentration (Cmax) appeared to be dose proportional for both the NK3RA and the active metabolite, up to approximately 80 mg. Renal elimination of the NK3RA or its metabolite was negligible. Following multiple dose administration, pharmacokinetic steady state was achieved within 4 days. At steady state, the exposure to the metabolite was approximately 66% of the parent circulated; the accumulation of the NK3RA in the plasma was minimal following QD dosing and was greater following BID dosing. NK3RA pharmacokinetics appeared to be time independent. Exposure to the NK3RA in patients with schizophrenia was similar to that seen in healthy subjects.

Food Effects and Formulation Development:

Bioavailability of tablet and liquid suspension formulations is similar. Based on limited observations, oral administration of the NK3RA suspension or tablets with food (a high-fat meal) increased the rate of absorption (suspension: 25% increase in Cmax; Tablet: 75% increase in Cmax).

Clinical—Endocrine Effects:

In healthy male volunteer subjects in both the SAD and MAD studies, the NK3RA demonstrated a dose dependent reduction in serum testosterone in both SAD and MAD studies with 1, 5, 10, 15, 40 and 80 mg tested in the SAD studies and 5 mg QD, 10 mg QD, 30 mg QD, 40 QD, 15 mg QD, 15 mg BID, or 30 mg BID tested in the MAD studies for up to 6 days.

In a phase II PoP schizophrenia trial using 40 mg QD, reduction in serum testosterone was also an observed effect.

Therefore we have consistently seen reductions in total testosterone levels durable up to 28 days dosing in male volunteers and male schizophrenia patients.

A Specific Example of a Pharmaceutical Preparation of NK3RA is as Follows:

The NK3RA may be formulated as a 20 mg white film-coated tablet and is compressed from granules containing 6.67% w/w of the NK3AR. The formulation may be comprised of a dual-filler combination of mannitol and microcrystalline cellulose, croscarmellose sodium as a disintegrant, hydroxypropyl cellulose as a binder, and sodium lauryl sulfate as wetting agent. Magnesium stearate may be used as a lubricant. The NK3RA is size reduced before incorporation into the granulation. Such a tablet formulation has been shown to have suitable compaction and dissolution properties for clinical study.

Clinical Information in Females with PCOS:

The pharmacodynamics, safety and pharmacokinetics of a compound of the present invention, NK3RA, is being further evaluated in a randomized, double-blind, placebo-controlled of NK3RA when given in multiple doses to females with PCOS.

In this type of clinical trial three doses of 20 mg once daily, 20 mg twice daily and 40 mg twice daily of test compound are being compared to placebo, and studied in parallel group design. The objectives of the study are to evaluate the changes from baseline of free and total testosterone on day 7 and 28 of dosing, to assess the safety and tolerability of the test compound in the target population, to measure the plasma exposure of the test compound and metabolite in the target population, and to assess the PK/PD relationship of the test compound and LH AUC, LH MPP and free and total testosterone. Exploratory analyses will focus on changes from baseline of LH, DHEA, FSH, oestrogen, progesterone, prolactin, thyroid stimulating hormone, Insulin-like Growth Factor 1 [IGF-1] (as surrogate for GH) and HbA1c on days 7 and 28, as well as the impact of treatment on patient reported outcomes and HRQoL as measured by change from baseline at day 28.

The study population includes women with PCOS aged 18-45. The study will enroll 14 PCOS subjects per dose cohort with a total of N=56 for the entire study (2 drop outs per group assumed to give 12 evaluable subjects per dose). Patients are being dosed in the study over a duration of 28 days.

| | Pre-screening | Screening | Baseline | Treatment | | | | Follow-up | Early Discontinuation |
|---|---|---|---|---|---|---|---|---|---|
| | | | | Visit number | | | | | |
| | | 1 | 2 | 3 | 4 | 5 | | 6 | 7 | 8 |
| | | | | Relative to baseline | | | | | |
| | −42 to −1 | −28 to −1 | −1 | +7 ± 1 | +14 ± 1 | +21 ± 1 | +28 ± 1 | +42 ± 3 | |
| Inclusion/exclusiom criteria | X | X | X | | | | | | |
| ICF issued | X | | | | | | | | |
| Informed consent | | X | | | | | | | |
| Demography | | X | | | | | | | |
| Medical/surgical history | | X | | | | | | | |
| HIV, Hep B, Hep C assessment | | X | | | | | | | |
| Test for alcohol and drugs of abuse | | X | | | | | | | |
| Randomisation | | | X | | | | | | |
| Dispense study medication (a) | | | X | | | | | | |
| Dispense dosing diary (b) | | | X | | | | | | |
| Administer morning dose at site with time recording (c) | | | | X | | | X | | |
| Assessment of compliance | | | | X | X | X | X | | |
| Return of unused medication | | | | | | | X | | |
| Record concomitant Medication | | X | X | X | X | X | X | X | X |
| Record Adverse Events (d) | | X | X | X | X | X | X | X | X |
| (Abbreviated) Physical exam | | X | | | | | X | X | X |
| Height | | X | | | | | | | |
| Weight | | X | X | X | | | X | X | X |
| BMI | | X | | | | | | | |
| Supine BP and HR (e) | | X | X | X | | | X | X | X |

|  | Pre-screening | Screening | Baseline | Treatment | | | | Follow-up | Early Discontinuation |
|---|---|---|---|---|---|---|---|---|---|
|  | | | | Visit number | | | | | |
|  | | 1 | 2 | 3 | 4 | 5 | 6 | 7 | 8 |
|  | | | | Relative to baseline | | | | | |
|  | −42 to −1 | −28 to −1 | −1 | +7 ± 1 | +14 ± 1 | +21 ± 1 | +28 ± 1 | +42 ± 3 | |
| 12 lead ECG (f) | | X | X | X | | | X | X | X |
| Urinalysis | | X | | | | | X | X | X |
| Urine pregnancy test | | X | X | X | X | X | X | X | X |
| HRQol - SF-36 | | | X | | | | X | | X |
| Symptoms questionnaire | | | X | X | X | X | X | | X |
| Haematology | | X | X | X | X | X | X | X | X |
| Clinical chemistry | | X | X | X | X | X | X | X | X |
| Screening Testosterone (total and free) | | X | | | | | | X | X |
| High frequency LH samples Every 10 mins for 8 hours (g) | | | X | X | | | X | | |
| Well defined testosterone (total and free), FSH. Hourly for 8 hours (h) | | | X | X | | | X | | |
| Single sample Testosterone (total and free, LH, FSH) | | | | | | | | X | X |
| Monitoring sample (i) Estradiol (E2), progesterone, prolactin, TSH, T4 (total and free) HbA1c, IGF-1 | | | X | X | | | X | X | X |
| Fast for 2 hours prior to and 1 hour post morning dose | | | | X | | | X | | |
| PK samples (j) | | | | X | | | X | | X |
| Pre dose 4-beta hydroxyl cholesterol and 6-beta hydroxyl testosterone | | | X | | | | X | | |
| Consent and blood sample for genetic analysis | | | | | | | X | | |

All labs central lab
(a) First dose to be taken as an outpatient on day 1
(b) For PK and PD measurements record dosing times on the day before the patient attends the site. Sites should contact subject by telephone to remind them
(c) Patient takes morning dose only on day 28
(d) SAEs will be recorded from signing of the informed consent, non-serious AEs will be recorded from the first administration of investigational product
(e) Measure BP and HR once patient has rested supine for 10 minutes
(f) On intensive monitoring days 7 and 28 take ECG 2 hours post dose
(g) LH sampling will be initiated at approximately the same time on each visit (±1 hour). Intensive sampling should begin by 9 am
(h) First sample pre-dose, within 30 minutes of dose
(i) Sample to be taken ±1 hour of same time each day for all visits
(j) PK sample times: Day 7 and 28: pre dose, 15 min, 30 min, 1 hour, 1.5, 2, 3, 4, 6, 8. Early discontinuation single sample.

Inclusion Criteria

For inclusion in the study subjects should fulfil the following criteria:
1. Provision of informed consent prior to any study specific procedures
2. female subjects between the ages of 18 to 45 years (inclusive)
3. Women has a diagnosis of polycystic ovary disease as defined by the following
   polycystic ovaries (previously documented ultrasound from records are acceptable)
   At screening free testosterone >ULN.
   At screening total testosterone <5 nmol/L
4. Amenorrhea or oligomenorrrhea (defined as <=6 menses per year)
5. Body Mass Index (BMI) between 18 and to 40 kg/m2 (inclusive)
6. Patient is permanently or surgically sterilized or who agrees to maintain abstinence for the duration of study participation, or who agrees to use/have their partner use effective methods of birth control for the duration of their study participation Permanent sterilisation includes bilateral salpingectomy but excludes bilateral tubal occlusion. Effective Methods of birth control within the study treatment period is defined as partner use of male condom plus one of: spermicide, vasectomy, tubal occlusion or an intrauterine device that does not contain steroid hormones.

Exclusion Criteria

Subjects should not enter the study if any of the following exclusion criteria are fulfilled:
1. Is peri-menopausal or has reached natural menopause—defined as FSH>10 IU/L
2. Has menstruated within the last month
3. Clinically relevant disease and abnormalities (past or present) which in the opinion of the investigator, may either put the subject at risk to participate in this study or may influence the results of the study or the subject's ability to participate in the study
4. Significant illness, as judged by the investigator, within 2 weeks of
   Day-1
5. Patient has clinical, laboratory, or ECG evidence of uncontrolled hypertension (defined as SBP of ≥160 mm Hg and/or DBP of ≥□100 mm Hg), uncontrolled diabetes, HIV disease, or significant pulmonary, renal, hepatic, endocrine, or other systemic disease in the opinion of the investigator
6. Subjects who have had a hysterectomy or bilateral oophorectomy or both; If the subject has had prior ovarian cystectomy(ies), unilateral oophorectomy, uterine surgery such as myomectomy(ies) or polypectomy(ies), etc., then these subjects may be considered on a case-by-case basis by the project Medical Advisor, with the aim to exclude anyone who no longer has ovarian function or a functional endometrium.
7. Patient has a history of Gilbert's syndrome, infectious hepatitis, or other significant hepatic disease (e. g. chronic hepatitis, cirrhosis, autoimmune hepatitis, primary sclerosing cholangitis, non-alcoholic steatohepatitis, or hereditary liver disease) in the opinion of the investigator.
8. Patient has a history of gastric or small intestinal surgery (including gastric bypass surgery or banding), or has a disease that causes malabsorption.
9. Clinically significant abnormal ECG and/or abnormalities in ECG as judged by the investigator at screening
10. A marked prolongation of QT/QTc interval (e.g., repeated demonstration of a QTc interval >450 milliseconds (ms))
11. A history of additional risk factors for TdP (e.g., heart failure, hypokalemia, family history of Long QT Syndrome)
12. The use of concomitant medications that prolong the QT/QTc interval
13. Positive human immune deficiency virus (HIV), Hepatitis B or Hepatitis C serology evaluations at the screening visit
14. Patient has a history of hypersensitivity to more than two chemical classes of drugs, including prescription and over-the-counter medications
15. Past (within 1 year of enrolment) or present alcohol or substance abuse or a positive test for alcohol or drugs of abuse or is a "recreational user" of illicit drugs or prescription medications
16. Positive test for drugs of abuse or alcohol at the screening visit
17. Patient consumes 3 or more alcoholic drinks per day. Note: 1 drink=12 oz. can/bottle of beer or 4 oz. of wine, or 1 oz. of liquor
18. Enrolment in another concurrent investigational study or intake of an investigational drug within 3 months or intake of an investigational drug within a period of 5 half lives of that drug prior to the screening visit
19. Blood loss in excess of 200 mL within 30 days of Day-1 in excess of 500 mL within 90 days of Day-1 or in excess of 1350 mL within 1 year of Day-1 or donation of blood products within 14 days of Day-1
20. Patient has a history of neoplastic disease <5 years prior to signing informed consent, except for adequately treated basal cell or squamous cell skin cancer or in situ cervical cancer.
21. Patient is pregnant (positive serum pregnancy test at anytime during study participation) or breast-feeding, or is a female expecting to conceive within the projected duration of the study
22. Involvement in the planning and/or conduct of the study (applies to both AstraZeneca staff and/or staff at the study site)
23. Inability to understand or cooperate with the requirements of the study
24. Patient is legally or mentally incapacitated
25. Patient has abnormal screening laboratory values as per the guidelines listed below or other clinically significant, unexplained laboratory abnormality according to the investigator.
   AST>1.5× upper limit of normal
   ALT>1.5× upper limit of normal
   Total bilirubin>1.5× upper limit of normal
   Serum creatinine>2.0× upper limit of normal
   DHEA and free testosterone upper limits
26. Patient has taken any of the following medications in the time frame specified:
4 Weeks Prior to Screening and Throughout the Study Period:
   Potent and moderate CYP3A4 inhibitors, including but not limited to: cyclosporine, systemic (oral/IV) itraconazole, ketoconazole, fluconazole, erythromycin, clarithromycin, telithromycin, nefazodone, HIV protease inhibitors, aprepitant, verapamil, diltiazem
   Potent and moderate CYP3A4 inducers, including but not limited to: rifampicin, rifabutin, carbamazepine, phenytoin, barbiturates, systemic glucocorticoids (replacements and inhaled are permitted), nevirapine, efavirenz, pioglitazone, primidone, St. John's wort
   Potent and moderate CYP2C9 inhibitors, including but not limited to amiodarone, fluconazole, miconazole, oxandralone:

Potent and moderate CYP2C9 inducers, including but not limited to: carbamazepine, rifampin Metformin 8 Weeks. Prior to Screening and Throughout the Study Period:

Oral contraception, Estrogen, Progestorone

Given the potential for a drug interaction between CYP3A4 substrates and NK3RA, the suitability of co-dosing and maximum dose of CYP3A4 inhibitors should be guided by approved label.

The use of concomitant medications that prolong the QT/QTc interval is prohibited.

Slight modifications to the trial proposal were made as the protocol evolved. For example in the original protocol the testosterone inclusion criteria was to be above the upper limit of normal but was eventually revised to free testosterone at screening greater than 85% of the age-specific upper limit of normal (ULN).

The effect of NK3RA on testosterone and LH is being assessed. Specifically, 8 hours of intensive LH sampling (1 sample per 10 min) at baseline and on day 7 and 28 was scheduled to capture changes of LH AUC and pulse frequency and amplitude over the dosing interval. LH pulse amplitude and frequency are mathematically modelled parameters from raw LH assay data. AUC is by definition a calculated entity influenced by frequency and amplitude, hence it is possible to infer information about LH pulsatility from LH AUC.

Hourly measurement of FSH and free and total testosterone was performed during these periods of intensive monitoring.

Plasma concentration-time profiles of NK3RA and its metabolite will be constructed for each subject in the PK Analysis Population. For each plasma concentration-time curve, the following PK parameters was determined using noncompartmental methods with validated PK software Cmax, time to maximum plasma concentration (Tmax), area under the curve (AUC0-8) for plasma concentration versus time curve.

Clinical safety and tolerability, are being assessed by changes in physical examinations, vital signs, body weight, clinical laboratory tests, adverse experiences, and electrocardiograms Results Interim data have been obtained from a total of 20 women with Polycystic Ovary Syndrome (PCOS) who received treatment (NK3RA or placebo) in the ongoing phase 2a study. This study is a 28 day, randomised, double blind placebo controlled study with 4 treatment arms, NK3RA 20 mg once daily, 20 mg twice daily, 40 mg twice daily and placebo in women with PCOS.

Tables 1 to 3 below summarise the number of patients with data supportive, consistent and not supportive by treatment group (placebo and NK3RA).

In Table 1 the criteria used to determine what is supportive, consistent or not supportive are based on a qualitative evaluation of the changes in:

(a) LH area under the curve (AUC) between 0 and 8 hours $AUC_{(0-8)}$ (b) LH pulsatility parameters derived through deconvolution (Veldhuis J D, Keenan D M, and Pincus S M. Motivations and methods for analyzing pulsatile hormone secretion. Endocrine Reviews. 2008, 29(7):823-864; and Liu P Y, Keenan D M, Kok P, Padmanabhan V, O'Byrne K T, and Veldhuis J D. Sensitivity and specificity of pulse detection using a new deconvolution method. Am J Physiol Endocrinol Metab. 2009; 297(2):538-44)

i) average mass per LH pulse in 8 hours ii) total number of LH pulses in 8 hours.

For LH, there is a relationship between the LH $AUC_{(0-8)}$ and LH pulsatility. In particular, reductions in LH $AUC_{(0-8)}$ that would be considered to be disease modifying in PCOS will manifest themselves in pulsatility parameters of average mass per LH pulse in 8 hours and/or total number of LH pulses in 8 hours. Mass per pulse (MPP) is defined the amount of LH released per reconstructed LH pulse. The LH $AUC_{(0-8)}$ can be more reliably measured compared to the pulsatility parameters and therefore why both $AUC_{(0-8)}$ and pulsatility are considered in interpreting the level of LH reduction.

| LH criteria for Table 1 | |
|---|---|
| Not supportive | Compared to baseline, LH AUC increases on either day 7 or 28 AND both MPP and number of pulses increase on either day 7 or 28 |
| Consistent | Compared to baseline, either LH AUC decreases on both days 7 and 28 OR either MPP or number of pulses decrease on both days 7 and 28 |
| Supportive | Compared to baseline, both LH AUC decreases on both days 7 and 28 AND either MPP or number of pulses decrease on both days 7 and 28 |
| Not evaluable | Insufficient data available to make a decision |

In Table 2 the criteria used to determine what is supportive, consistent or not supportive are based on a qualitative evaluation of the changes in average (on an individual patient basis) free testosterone.

In Table 3 the criteria used to determine what is supportive, consistent or not supportive are based on a qualitative evaluation of the changes in average (on an individual patient basis) total testosterone.

| Free T/Total T (evaluated independently) for Tables 2 and 3 | |
|---|---|
| Not supportive | Compared to baseline, there is an increase in testosterone on both days 7 and 28 |
| Consistent | Compared to baseline, there is a decrease in testosterone on either days 7 and 28 |
| Supportive | Compared to baseline, there is a decrease in testosterone on both days 7 and 28 |
| Not evaluable | Insufficient data available to make a decision e.g. baseline is missing |

Expert judgement was necessary in the application of these criteria and therefore plots were evaluated independently by 3 AZ physicians. The most common result across the 3 physicians determined provided the overall evaluation for a single patient. These criteria were agreed between the 3 reviewers ahead of the plots being available for review.

TABLE 1

| | No. of patients | | |
|---|---|---|---|
| LH | Supportive | Consistent | Non-supportive |
| NK3RA | 2 | 3 | 3 |
| Placebo | 0 | 1 | 1 |
| Total | 2 | 4 | 4 |

TABLE 2

| Free testosterone | No. of patients | | |
|---|---|---|---|
| | Supportive | Consistent | Non-supportive |
| NK3RA | 2 | 4 | 3 |
| Placebo | 0 | 1 | 1 |
| Total | 2 | 5 | 4 |

TABLE 3

| Total Testosterone | No. of patients | | |
|---|---|---|---|
| | Supportive | Consistent | Non-supportive |
| NK3RA | 3 | 3 | 4 |
| Placebo | 0 | 0 | 3 |
| Total | 3 | 3 | 7 |

Only the number of patients with data that were evaluable for the relevant parameter is recorded in the tables. Some data were not evaluable, because the pre dose baseline was missed or samples were missing or haemolysed during the 8 hour profile.

Example 1

3-(Methanesulfonamido)-2-Phenyl-N-[(1S)-1-Phenylpropyl]Quinoline-4-Carboxamide Having the Following Structure May be Prepared as Follows

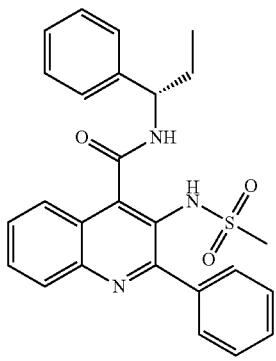 [SMILES: CC[C@H](NC(=O)c1c(NS(C)(=O)=O)c(-c2ccccc2)nc2ccccc12)c1ccccc1]

To 3-[(methylsulfonyl)amino]-2-phenylquinoline-4-carboxylic acid (1c) (20.00 g, 58.4 mmol) in ethyl acetate (180 ml) 1,1'-carbonyldiimidazole (13.26 g, 81.8 mmol) is added. The resulting slurry is heated to 50° C. and the reaction mixture stirred at 50° C. for 6 h. (S)-(−)-1-phenylpropylamine (11.85 g, 87.6 mmol) in ethyl acetate (15 ml) is then added and the reaction mixture further heated to 70° C. and stirred for 8 h. The solution is then cooled to room temperature and the residue partitioned between ethyl acetate and aqueous hydrochloric acid. The organic phase is then co-distilled with isopropanol to result in an isopropanol solution. This is then seeded and cooled. The solid is collected by filtration, washed with isopropanol and dried to yield the title compound (19.74 g, 74%) as a solid. $^1$H NMR (300 MHz, CDCl$_3$) δ 0.94 (t, 3H), 1.97 (m, 2H), 3.44 (s, 3H), 5.17 (q, 1H), 5.47 (m, 2H), 7.32 (d, 2H), 7.34 (d, 2H), 7.39 (m, 1H), 7.78 (m, 2H), 7.84 (m, 2H), 8.08 (m, 1H), 8.30 (m, 2H), 8.42 (m, 2H). MS APCI, m/z=460 (M+1).

The starting acid, 3-[(methylsulfonyl)amino]-2-phenylquinoline-4-carboxylic acid (1c), may be prepared in the following manner:

N-(2-oxo-2-phenylethyl)methanesulfonamide (1b)

A solution of 2-amino-1-phenylethanonehydrochloride (200 g, 1.165 mol) in NMP (800 mL) is formed and after cooling, methylsulfonyl chloride (117.3 mL, 1.515 mol) is added slowly. This is followed by the slow addition of N-methylmorpholine (450.1 ml, 4.078 mol), the reaction mixture is then stirred at 0° C. for 1 h. The mixture is warmed, with brine and seed then being added. The result slurry is cooled and solid collected by filtration, washed with water and dried to yield the title compound (209.9 g, 85%) MS APCI, m/z=214 (M+1).

3-[(methylsulfonyl)amino]-2-phenylquinoline-4-carboxylic acid (1c)

A slurry of N-(2-oxo-2-phenylethyl)methanesulfonamide (1b) (100 g, 0.469 mol) and isatin (69 g, 0.469 mol) in isopropanol (700 ml) is heated to 50° C. Aqueous sodium hydroxide (133 ml, 2.334 mol) is added. The reaction mixture is heated to 75° C. and stirred for 1 h. The resulting solution is cooled and acidified with hydrochloric acid to pH4. The solution is seeded and further hydrochloric acid added to achieve pH2-3. The resulting solid is collected by filtration, washed with isopropanol and water and dried to yield the title compound (112.1 g, 65%). $^1$H NMR (300 MHz, CDCl$_3$) δ 3.11 (s, 3H), 7.05 (d, 1H), 7.39 (d, 2H), 7.64 (m, 2H), 7.78 (m, 1H), 8.06 (m, 1H), 8.19 (m, 1H), 8.47 (m, 1H), 10.03 (b, 2H). MS APCI, m/z=343 (M+1).

Example 2

Method:

Population pharmacokinetic/pharmacodynamic (PK/PD) modeling of NK3RA and testosterone concentrations from four phase I studies and one phase II study was performed to quantify the exposure-response relationships between plasma concentrations of NK3RA and testosterone. PKPD analyses were conducted using sequential approach via nonlinear mixed-effects modeling with NONMEM® VII. The PK model was developed first and the predicted concentrations from the empirical Bayes estimates of the PK parameters were used in the PD response model building. The developed PKPD model was used to explore different dosing regimens [40 mg bi-daily (BID) vs 80 mg once-daily (QD)] targeting reduction of plasma testosterone levels and predict PD response.

NONMEM is a software package, just like Microsoft Office. It is a specialized software for the analysis of pharmacokinetic and pharmacodynamic data. NONMEM is an abbreviation of the full name "NONlinear Mixed-Effect Modeling" which was developed at the University of California at San Francisco by two professors, Lewis Sheiner and Stuart Beal in the late 1970s and has become the "gold standard", both in the pharmaceutical industry and academia.

The NONMEM software is a regression program that specializes in non-linear systems. The population PK analysis was based on multiple regression using non-linear mixed effect models. Mixed effect models describe the influence of both fixed effects and random effects on a dependent variable, e.g. plasma drug concentration or a clinical endpoint. Fixed effects, THETA (θ) in NONMEM notation, are factors that are either measured or controlled, e.g. CL and V. Random effects include residual error (ERR), epsilon (ε) in NONMEM notation, and between subject random effects, ETA (η) in NONMEM notation.

Population PK mixed effects models typically include four basic components: the structural PK model, which predicts the plasma concentration as a function of time and dose; the covariate model component, which describes the influence of fixed effects (e.g. demography) on PK model population parameters; the between-subject variance component, which describes the inter-individual variation in PK parameters (after "correction" for fixed effects); and the residual error model components, which describes the underlying distribution of the error in the measured PK variable.

Figure 2:
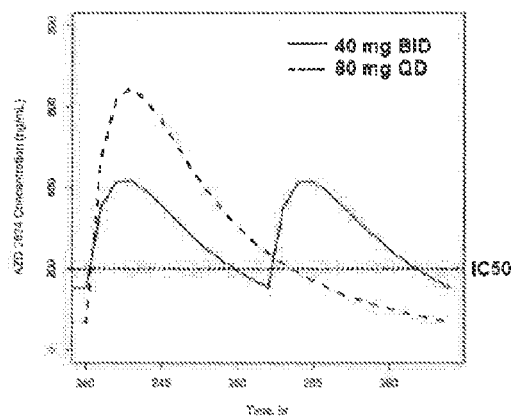
FIG. 2 is the predicted steady state NK3RA concentration after administering 40 mg BID or 80 mg QD of NK3RA (Note: the mean weight of subjects in the simulation dataset is same as the mean from the present study cohorts at 77 Kg).
Figure 3:
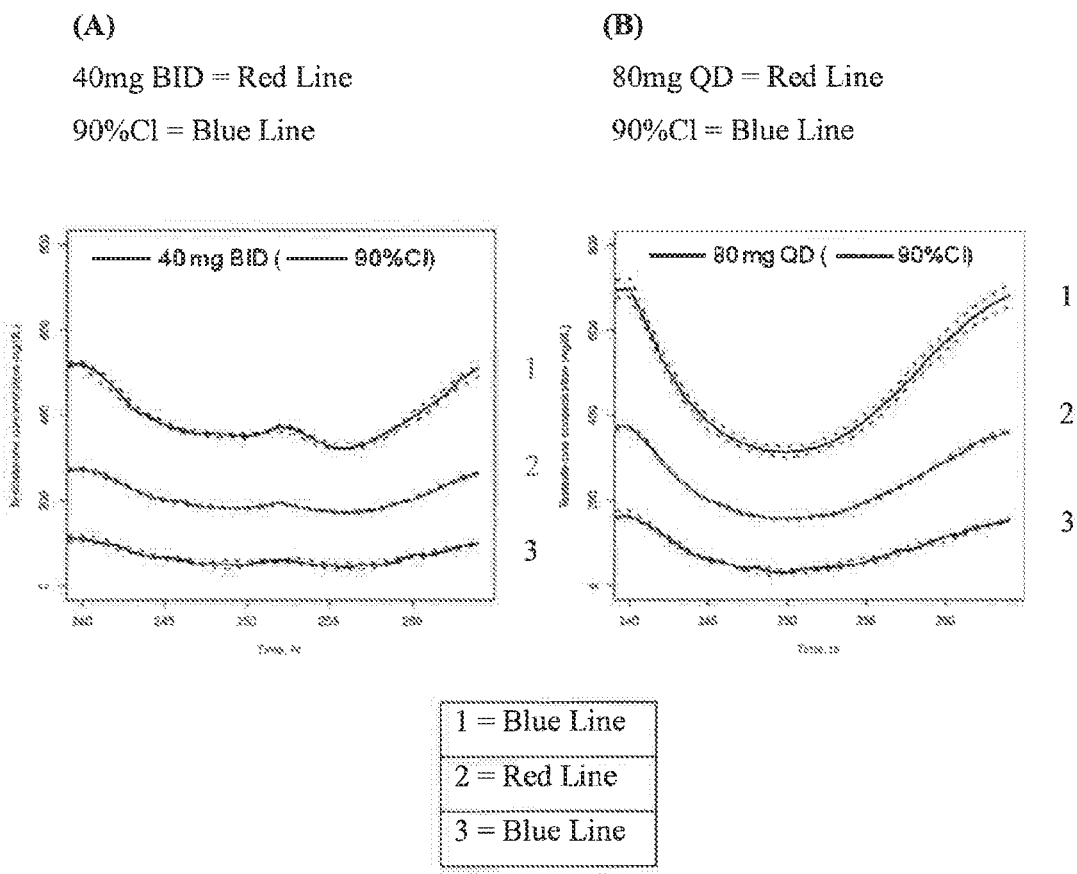
FIG. 3 is the predicted steady state testosterone concentration after administering 40 mg BID or 80 mg QD of NK3RA.

Results:

Data including 3597 NK3RA PK observations and 786 testosterone concentrations from 139 healthy volunteers were investigated. A two-compartment model with first-order elimination best described NK3RA PK. Circadian rhythm of baseline testosterone concentrations was well described by a cosine function. Indirect response model (inhibition on testosterone production) was used to link the drug effect to PD response. The scheme of PKPD model is illustrated in FIG. 1. It was concluded that following 40 mg BID treatment, trough NK3RA concentration will be higher compared to 80 mg BID. The time above IC50 for testosterone concentration after 40 mg BID of NK3RA is 80.9% time of the dosing interval compared to only 55.7% after 80 mg QD (FIG. 2). The mean predicted peak testosterone concentration at steady state are lower and overall less variable during 24 hrs for 40 mg BID dose compared to 80 mg QD dose (FIG. 3). These findings surprisingly suggest 40 mg BID dosing provided better sustained testosterone suppression effect during dose interval than 80 mg QD.

Conclusions:

Population pharmacokinetic and pharmacodynamic analysis demonstrates that 40 mg administered twice a day is better than 80 mg once a day to maximally suppress testosterone during the entire dosing interval.

The invention claimed is:
1. A pharmaceutical composition comprising:
3-(methanesulfonamido)-2-phenyl-N-[(1S)-1-phenylpropyl]quinoline-4-carboxamide (NK3RA) or a pharmaceutically acceptable salt thereof;
mannitol and microcrystalline cellulose;
croscarmellose sodium;
hydroxypropyl cellulose;
sodium lauryl sulphate; and
magnesium stearate.

* * * * *